United States Patent [19]

Merchant et al.

[11] Patent Number: 5,430,206
[45] Date of Patent: Jul. 4, 1995

[54] METHOD FOR PURIFYING DICHLOROPENTAFLUOROPROPANES

[75] Inventors: Abid N. Merchant, Wilmington, Del.; Allen C. Sievert, Elkton, Md.

[73] Assignee: E. I. Du Pont de Nemours and Company, Wilmington, Del.

[21] Appl. No.: 784,672

[22] Filed: Oct. 25, 1991

Related U.S. Application Data

[63] Continuation of Ser. No. 615,911, Nov. 20, 1990, abandoned.

[51] Int. Cl.$^6$ ............................................. C07C 17/38
[52] U.S. Cl. ................................. 570/178; 570/177
[58] Field of Search ...................... 570/172, 178, 177

[56] References Cited

U.S. PATENT DOCUMENTS

| | | | |
|---|---|---|---|
| 2,450,414 | 10/1948 | Benning | 570/178 |
| 2,462,402 | 2/1949 | Joyce | 570/172 |

FOREIGN PATENT DOCUMENTS 616096  3/1961  Canada ................................. 570/178

OTHER PUBLICATIONS

Coffman et al., J. Amer. Chem. Soc., vol. 71, pp. 979–990 (1949) "Synthesis of Chlorofluoropropanes".
Siegel et al., J. Org. Chem., 53 pp. 2629–2630 (1988) "Dichlorofluoromethane-d: A Versatile Solvent for VT-NMR Experiments".
Boothe et al., Ind. and Eng. Chem. vol. 24 pp. 637–641 (Jun. 1932) "Fluorine Derivatives of Chloroform".

*Primary Examiner*—Alan Siegel
*Attorney, Agent, or Firm*—Michael K. Boyer

[57] ABSTRACT

A method of recovering pure dichloropentafluoropropane from a mixture of dichloropentaflouropropane and chloroform (including breaking the azeotropic mixture thereof) involving selectively fluorinating the chloroform to the lower boiling dichloromonofluoromethane and then distilling to separate and recover pure dichloropentafluoropropane.

16 Claims, No Drawings

METHOD FOR PURIFYING DICHLOROPENTAFLUOROPROPANES

This application is a continuation of application Ser. No. 07/615,911 filed Nov. 20, 1990, now abandoned.

BACKGROUND OF THE INVENTION

1. Field of the Invention

The present invention relates to a method of separating mixtures of dichloropentafluoropropanes, $C_3HCl_2F_5$, from chloroform, $CHCl_3$, (including but not limited to azeotropic mixtures) and recovering purified dichloropentafluoropropanes. More specifically, but not by way of limitations, the present invention relates to the selective fluorination of chloroform in the presence of dichloropentafluoropropanes to lower boiling fluorinated products (e.g., dichloromonofluoromethane) followed by separating the fluorinated products (e.g., by distillation) from the dichloropentafluoropropanes.

2. Description of Related Art

Advances in modern technology, particularly in the electronic areas, depend upon cleanliness of the various components. For example, in the manufacture of the electronic circuit boards, with their increased circuitry and component densities, thorough and effective cleaning of the boards after soldering is of utmost importance. At the present time, for the most part, cleaning of such articles is done by solvent washing utilizing various solvents and processes.

The solvent of choice at the present time is 1,1,2-trichloro-1,2,2-trifluoroethane (CFC-113) because this solvent provides the essential characteristics required of an effective washing solvent such as convenient atmospheric boiling point, non-flammability, low toxicity, inertness to various materials of construction, high stability, and high solvency. CFC-113 is often used with small amounts of co-solvents such as acetone or methanol to enhance certain solvency characteristics.

In recent years, however, CFC-113 has been suspected of contributing to the depletion of the stratospheric ozone layer. Because of its unusual high stability, it is believed that CFC-113 remains intact in the earth's atmosphere and then upon reaching the stratosphere undergoes decomposition and the decomposition products participate in the ozone layer depletion process.

In a pending U.S. patent application Ser. No. 07/422,012 filed Oct. 16, 1989, which corresponds to WIPO publication number WO91/05753, it has been proposed that each of isomeric hydrodichloropentafluoropropanes or mixtures thereof represented by the formula $C_3HCl_2F_5$ are suitable substitutes for CFC-113. These chlorofluoropropanes include $CHClFCClFCF_3$ (HCFC-225ba, b.p. 56.0° C.), $CHF_2CClFCClF_2$ (HCFC-225bb, b.p. 56.3° C.), $CHCl_2CF_2CH_3$ (HCFC-225ca, b.p. 53.0° C.), $CHClFCF_2CClF_2$ (HCFC-225cb, b.p. 52.0° C.), and $CClF_2CHClCF_3$ (HCFC-225da, b.p. 50.4° C.). These chlorofluoropropanes have characteristics very similar to those of CFC-113, such as relatively low boiling points, non-flammability, low toxicity, inertness to various materials of construction, high solvency and in-use stability, but are believe to have little or no stratospheric ozone layer depletion potential. It is now generally believed that hydrogen-containing chlorofluorocarbons (HCFCs) undergo decomposition reactions, such as dehydrochlorination, in the atmosphere such that the compounds do not survive to reach the stratosphere and thus should have little effect upon the ozone layer depletion process.

One of the ways whereby hydrochlorofluoropropanes of the formula $C_3HCl_2F_5$ can be prepared is by reaction of dichlorofluoromethane, $CHCl_2F$ (HCFC-21), with tetrafluoroethylene, $CF_2=CF_2$, in the presence of an aluminum halide catalyst as represented by the following equation:

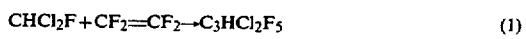

$$CHCl_2F + CF_2=CF_2 \rightarrow C_3HCl_2F_5 \qquad (1)$$

wherein "$C_3HCl_2F_5$" represents an isomeric mixture of hydrogen-containing chlorofluoropropanes. The reaction of $CHCl_2F$ with $CF_2=CF_2$ to produce these chlorofluoropropanes has been disclosed by Joyce in U.S. Pat. No. 2,462,402, by Coffman et al. in *J. Amer. Chem. Soc.*, Vol. 71, pp 979–980 (1949), and by Paleta et al. in *Coll. Czech. Chem. Comm.*, Vol. 35, pp 1867–1875 (1971).

One of the complications of the reaction shown in equation (1) is the concomitant production of chloroform, $CHCl_3$, by the aluminum halide-catalyzed disproportionation of HCFC-21 or by the chlorination of HCFC-21 by the catalyst. The reaction products may contain as high as 30 mole % chloroform. In many applications, it may be desirable to have pure dichlorofluoropropane in the formulations, thus the chloroform must be removed. Theoretically, since chloroform boils at 61.2° C., some 5° higher than the highest boiling dichloropentafluoropropane, separations should be possible by careful distillation. However, and as made the subject of a U.S. patent application Ser. No. 07/615,912 filed concurrently herewith, chloroform forms azeotropes with most of the $C_3HCl_2F_5$ isomers. For example, it has now been discovered that a mixture of HCFC-225 isomers consisting of HCFC-225ca, HCFC-225aa and HCFC-225cb in a 10.4:1.0:8.6 mole ratio forms a true azeotrope with chloroform. This azeotrope contains 79.8 wt. % dichloropentafluoropropane and 20.2 wt. % chloroform and boils at atmospheric pressure at 51.2° C. Similarly, the individual isomers HCFC-225cb and HCFC-225ca at 71.5 wt. % and 83.6 wt. % with chloroform are established as true binary azeotropes boiling at 53.9° and 50.9° C., respectively. The presence of the azeotropes make the separation of the chloroform by distillation impractical.

SUMMARY OF THE INVENTION

In view of the difficulties associated with isolating pure dichloropentafluoropropane from chloroform, the present invention provides a method for recovering purified dichloropentafluoropropane from a mixture of dichloropentafluoropropane and chloroform. The method according to the present invention involves selectively fluorinating the chloroform in the presence of the dichloropentafluoropropane by use of a fluorinating agent or catalyst followed by removal of the lower boiling fluorination products from the dichloropentafluoropropane (i.e., evaporation, distillation, refluxing, vaporization, flashing or the like). In this manner, substantially pure dichloropentafluoropropane is recovered.

Thus, the present invention provides a method of purifying dichloropentafluoropropane comprising the steps of:

(a) contacting a mixture of dichloropentafluoropropane and chloroform with an effective amount of a fluorinating agent to convert at least a portion of said chloroform to a product containing at least one fluorine substituent; and (b) recovering purified dichloropentafluoropropane.

Preferably the recovery of purified dichloropentafluoropropane is by distillation which can be effective even if the starting mixture is azeotropic or would have formed an azeotrope upon distillation.

It is an object of the present invention to provide a method of recovering purified dichloropentafluoropropanes from mixtures involving dichloropentafluoropropanes and chloroform, including azeotropic mixtures or mixtures that would inherently produce the azeotrope during distillation, evaporation or reflux. It is a further object of the present invention to provide such a process by selectively fluorinating the chloroform in the mixture to lower boiling products such that subsequent distillation will separate and recover the desired pure dichloropentafluoropropanes. Fulfillment of these objects will be apparent upon complete reading of the specification and attached claims.

DESCRIPTION OF THE PREFERRED EMBODIMENTS

According to the present invention, purified dichloropentafluoropropane can be obtained from a mixture of dichloropentafluoropropane and chloroform by first treating the mixture with a fluorinating agent and then effecting the separation and recovery of dichloropentafluoropropane by distillation. Further according to the present invention, it has been discovered that treating the mixture with a fluorinating agent will selectively convert the chloroform to lower boiling fluorinated products represented by dichloromonofluoromethane (HCFC-21, b.p. 8.9° C.) and monochlorodifluoromethane (HCFC-22, b.p. −40.7° C.) without significantly fluorinating the dichloropentafluoropropane. The low boiling chlorofluoromethanes produced by the selective fluorination can be removed easily from the higher boiling dichloropentafluoropropane (e.g., by fractional distillation or equivalent separation technique) to provide purified dichloropentafluoropropane.

It should be appreciated that for purposes of the present invention the term dichloropentafluoropropane refers to any of the HCFC-225, $C_3HCl_2F_5$, isomers as well as mixtures of these isomers and in particular includes azeotrope-forming compounds (i.e., form an azeotrope with chloroform). It should be further appreciated that the mixture of dichloropentafluoropropane and chloroform referred to in the present invention can include the presence of other additional inert or chemically passive additives, compounds or agents, provided that other compounds and any products derived therefrom by the fluorination step do not interfere with the subsequent separation and recovery of the dichloropentafluoropropane.

The fluorination of chloroform to form chlorofluoromethanes is generally well known in the art. Thus the use of the term "fluorinating agent" for purposes of this invention includes any fluorination agent as generally known in the art to fluorinate chloroform. Such fluorinating agents include, by way of example but not limited thereto:

(1) antimony trifluoride preferably in the presence of antimony pentachloride,
(2) antimony pentafluoride,
(3) antimony chlorofluorides of the general formula $SbCl_{5-x}F_x$ where X is preferably 1 or more,
(4) metal fluorides such as KF, NaF, AgF, $HgF_2$, $TaF_5$, $NbF_5$, and the like,
(5) hydrogen fluoride alone or in the presence of catalytic amounts of $SbCl_5$, a mixture of $SbCl_3$ and $SbCl_5$, $AlF_3$, $CrF_3$, $FeCl_3$, $SnCl_4$, $MoCl_5$, $WCl_6$, $TiCl_4$, $HfCl_4$, $TaF_5$, $NbF_5$, and the like.

The preferred fluorination agent is antimony pentachloride and HF since this system is used commercially in the manufacture of chlorofluorocarbons.

While vapor phase fluorination processes to fluorinate chloroform can be used, for convenience and simplicity the preferred process is a liquid phase fluorination process. For smaller scale operations, treatment of the dichloropentafluoropropane/chloroform mixture with antimony trifluoride in the presence of a catalyst such as antimony pentachloride is preferred. Bromine or chlorine could also be added to the antimony trifluoride to generate the antimony pentafluoride in situ. The amount of fluorination agent to be used should be at least the amount necessary to replace at least one chlorine atom of the chloroform with fluorine, but for ease of reaction and to remove as much of the chloroform as possible, the amount of fluorination agent should be from about 2 to 10 times the minimum required.

The success of the present purification process is based upon the discovery that the fluorination of chloroform takes place much more readily than the fluorination of dichloropentafluoropropane such that all or substantially all of the chloroform is fluorinated before any appreciable amount of dichloropentafluoropropane is fluorinated.

Fluorination pressure is not critical and can be atmospheric or superatmospheric depending upon the nature of the fluorination agent used. Since the fluorination is preferably carried out in the liquid state, and since dichloropentafluoropropanes boil at about 50° C., and particularly when hydrogen fluoride is a part of the fluorination agent, the fluorination pressure is preferably superatmospheric.

Illustrative of the process of the present invention, a mixture of dichloropentafluoropropane and chloroform is contacted with, for example, a mixture of $SbF_3$ and $SbCl_5$ in a reaction vessel. Such reaction vessel may be at atmospheric pressure suitably equipped with a reflux condenser or a closed vessel whereas autogenous pressure is allowed to develop. The mixture is then heated for a short period and distilled to obtain purified dichloropentafluoropropane essentially free of chloroform°

The following examples are presented to further illustrate specific embodiments of the present invention.

EXAMPLE 1

A 500 mL three-neck flask was equipped with a mechanical stirrer, a reflux condenser cooled by a circulating liquid to 5° C., and an additional funnel. $SbF_3$ (118 g, 0.66 mole) and $SbCl_5$ (45 g, 0.15 mole) were placed in the reaction flask. To the stirred mixture of antimony halides, 198 g of a mixture of chloroform and dichloropentafluoropropanes (a mixture of HCFC-225ca and HCFC-225cb) containing approximately 13% chloroform by weight was added over a period of 0.5 hours via the addition funnel. The reaction mixture was then stirred for 0.25 hours and gradually heated to about 50° C. and kept at that temperature for about 2 hours. The contents of the reaction vessel were then distilled, the distillate washed with water (2×100 mL), and dried over anhydrous $Na_2SO_4$. The resulting dichloropentafluoropropane weighed 126.7 g; GC analysis indicated that the product contained about 0.07% by weight chloroform.

EXAMPLE 2

56.3 g of a mixture HCFC-225 isomers (i.e., HCFC-225ca and HCFC-225cb) containing about 4 weight percent chloroform were dried over anhydrous sodium sulfate and added to a 100 mL three-neck round bottom flask. The flask was equipped with a "TEFLON"-coated stirring bar, a thermocouple, a reflux condenser cooled by a circulating liquid to 3° C., and an addition funnel. SbF$_5$ (5 g, 0,023 mole) was placed in the additional funnel and added to the rapidly stirred solution in several portions at ambient temperature; a 6° C. exotherm was observed. The reaction mixture was then stirred for 0.5 hours. The reflux condenser was then replaced with a short distillation column and distillation head. The HCFC-225 isomers were then distilled out of the flask at a temperature of 49° to 54° C. to afford 43.5 grams of clear liquid. No chloroform was detected in the product by GC analysis. A full analysis of the starting material and distilled product is given in the following Table I.

TABLE I

| Component | Starting Material | Product |
|---|---|---|
| HCFC-225ca/aa | 69.7 | 75.8 |
| HCFC-225cb | 23.6 | 22.6 |
| CFC-215cb | 2.5 | 0.9 |
| CFC-215ca | 0.3 | 0.1 |
| CHCl$_3$ | 2.8 | 0.0 |
| HCFC-224's | 0.8 | 0.0 |

EXAMPLE 3

SbCl$_5$ (8 g, 0,027 mole) was placed in a 150 mL stainless steel cylinder along with a "TEFLON"-coated magnetic stirring bar. The cylinder was attached to a metal vacuum line, cooled to $-196°$ C. in liquid nitrogen and HF (19.3 g, 0.97 mole) was transferred into the flask. The cylinder was warmed to room temperature and stirred for about 1 hour.

The cylinder was then cooled to $-196°$ C., evacuated, and 40 grams of a mixture of HCFC-225 isomers (i.e., HCFC-225ca and HCFC-225cb) containing about 0.9 weight percent CHCl$_3$ was added. The cylinder was warmed to 50° C. and held at 47°–61° C. for about 2 hours. The cylinder was then cooled back to $-196°$ C. and evacuated, and the volatile products were distilled out of the reactor and washed with water. Analysis of this product revealed only a trace of chloroform.

EXAMPLE 4

A five liter four neck, round-bottom flask was charged with 4959 grams of a mixture of HCFC-225's and chloroform containing 0.97 mole percent chloroform (28.4 g, 0.238 mole). The flask was fitted with an addition funnel, a mechanical stirrer, a thermocouple, and a reflux condenser. The reflux condenser was connected to a nitrogen bubbler through a $-78°$ C. trap. This trap served to condense HCFC-21 vapor coming out of the reaction.

The addition funnel was charged with 120 grams (0.554 mole) of SbF$_5$. As the reaction was stirred at ambient temperature, the SbF$_5$ was added dropwise over the course of about 1.3 hours. During the course of the addition, the reaction became steadily darker; no exotherm was detected. The black reaction mixture was allowed to stand overnight.

The reaction mixture was then treated with 1.5 liters of 6 molar HCl with rapid stirring; a 4° C. heat kick was observed. The lower layer was withdrawn from the reaction flask and washed consecutively with 1.5 liters of 6 molar HCl, 1.5 liters of 5% NaHCO$_3$, and then 2 liters of water. The resulting brown organic product was dried over CaSO$_4$. No chloroform was detected in the product by either GC of 1H NMR. A full analysis of the starting material and product is given in Table II.

TABLE II

| Component | Starting Material | Product |
|---|---|---|
| HCFC-225ca | 82.6 | 83.0 |
| HCFC-225aa | 5.6 | 5.8 |
| HCFC-225cb | 8.3 | 8.6 |
| HCFC-225ba* | 2.6 | 2.7 |
| CHCl$_3$ | 1.0 | 0.0 |

*both diastereomers

EXAMPLE

SbCl$_5$ (4.78 g, 0.016 mole) and SbF$_5$ (0.86 g, 0.0040 mole) were placed in a 150 ml stainless steel cylinder along with a "TEFLON"-coated magnet stirring bar. The cylinder was attached to a metal vacuum line, cool to $-78°$ C. in dry ice-methanol, evacuated and warmed to ambient temperature. 200 psig of nitrogen were added to the cylinder and the cylinder was then warmed to 98°–99° C. and stirred for about 1 hour.

The cylinder was then cooled to $-196°$ C. in liquid nitrogen and evacuated. A mixture of HCFC-225 isomers (50 g, 0.246 mole) and chloroform (1 g, 0.0084 mole) was condensed into the cylinder in vacuo. The cylinder was warmed to ambient temperature and pressurized with 200 psig of nitrogen and then heated to 97°–102° C. for 2 hours.

The cylinder was then cooled back to $-78°$ C. and carefully vented. The water-washed organic products recovered from the cylinder weighed 42.2 grams. The GC analysis of the starting material and product is given in the Table III.

TABLE III

| Component | Starting Material | Product |
|---|---|---|
| HCFC-225ca/aa | 57.9 | 57.9 |
| HCFC-225cb | 41.1 | 41.0 |
| HCFC-22 | 0.0 | 0.1 |
| HCFC-21 | 0.0 | 0.1 |
| HCFC-123(?) | 0.0 | 0.1 |
| CFC-131 | 0.0 | 0.2 |
| CHCl$_3$ | 1.0 | 0.4 |

Having thus described and exemplified the invention with a certain degree of particularity, it should be appreciated that the following claims are not to be so limited but are to be afforded a scope commensurate with the wording of each element of the claim and equivalents thereof.

We claim:

1. A method of purifying dichloropentafluoropropane comprising the steps of:
   (a) contacting a mixture of dichloropentafluoropropane and chloroform with an effective amount of a fluorinating agent at a temperature less than about the boiling point of dichloropentafluoropropane, and for a time sufficient to selectively convert at least a portion of said chloroform to a product containing at least one fluorine substituent;

(b) separating said product from the dichloropentafluoropropane and;

(c) recovering purified dichloropentafluoropropane.

2. A method of claim 1 wherein said contacting is in the liquid phase and said separating is by distillation.

3. A method of claim 1 wherein said fluorinating agent is selected from the group consisting of:
antimony trifluoride in the presence of antimony pentachloride;
antimony pentafluoride;
antimony chlorofluorides of the general formula $SbCl_{5-x}F_x$ where X is 1 or more;
metal fluorides KF, NaF, AgF, HgF$_2$, TaF$_5$, or NbF$_5$; and
hydrogen fluoride alone or in the presence of catalytic amounts of SbCl$_5$, a mixture of SbCl$_3$ and SbCl$_5$, AlF$_3$, CrF$_3$, FeCl$_3$, SnCl$_4$, MoCl$_5$, WCl$_6$, TiCl$_4$, ZrCl$_4$, HfCl$_4$, TaF$_5$, or NbF$_5$.

4. A method of claim 2 wherein said fluorinating agent is selected from the group consisting of:
antimony trifluoride in the presence of antimony pentachloride;
antimony pentafluoride;
antimony chlorofluorides of the general formula $SbCl_{5-x}F_x$ where X is 1 or more;
metal fluorides KF, NaF, AgF, HgF$_2$, TaF$_5$, or NbF$_5$; and
hydrogen fluoride alone or in the presence of catalytic amounts of SbCl$_5$, a mixture of SbCl$_3$ and SbCl$_5$, AlF$_3$, CrF$_3$, FeCl$_3$, SnCl$_4$, MoCl$_5$, WCl$_6$, TICl$_4$, ZrCl$_4$, HfCl$_4$, TaF$_5$, or NbF$_5$.

5. A method of claim 1 wherein said contacting is performed in the presence of a catalyst.

6. A method of claim 5 wherein said fluorinating agent comprises antimony trifluoride and said catalyst comprises antimony pentachloride.

7. A method of claim 1 wherein said separating comprises a process selected from the group consisting of distilling, evaporating, refluxing, vaporizing, and flashing.

8. A method of claim 1 wherein said mixture comprises an azeotrope of dichloropentafluoropropane and chloroform, and said separating comprises a process selected from the group consisting of distilling, evaporation, and refluxing.

9. A method for purifying dichloropentafluoropropane comprising the steps of:
(a) contacting an azeotrope mixture comprising dichloropentafluoropropane and chloroform with an effective amount of a fluorinating agent at a temperature less than about the boiling point of said dichloropentafluoropane, and for a time sufficient to convert at least a portion of said chloroform to a product having a lower boiling point than said dichloropentafluoropropane, (b) separating said product from the mixture and;

(c) recovering said dichloropentafluoropropane.

10. A method for isolating dichloropentafluoropropane comprising the steps of:
(a) contacting a mixture comprising dichloropentafluoropropane and chloroform with an effective amount of a fluorinating agent, at a temperature less than about the boiling point of said dichloropentafluoropropane, for a time sufficient to convert at least a portion of said chloroform to a product comprising at least one fluorine substituent, without significantly fluorinating the dichloropropane and;

(b) recovering said dichloropentafluoropropane.

11. The method of claim 9 wherein said contacting is performed while in the presence of a catalyst.

12. The method of claim 10 wherein said contacting is performed while in the presence of a catalyst.

13. The method of claim 11 wherein said recovering comprises a process selected from the group consisting of distilling, evaporating, refluxing, vaporizing, and flashing.

14. The method of claim 10 wherein said mixture comprises an azeotrope.

15. A method of claim 9 wherein said fluorinating agent comprises a member selected from the group consisting of:
antimony trifluoride in the presence of antimony pentachloride;
antimony pentafluoride;
antimony chlorofluorides of the general formula $SbCl_{5-x}F_x$ where X is 1 or mixture of SbCl$_3$ and SbCl$_5$, AlF$_3$, CrF$_3$, FeCl$_3$, SnCl$_4$, MoCl$_5$, WCl$_6$, more; metal fluorides KF, NaF, AgF, HgF$_2$, TaF$_5$, or NbF$_5$; and
hydrogen fluoride along or in the presence of catalytic amounts of SbCl$_5$, a TICl$_4$, ZrCl$_4$, HfCl$_4$, TaF$_5$, or NbF$_5$.

16. A method of claim 10 wherein said fluorinating agent comprises a member selected from the group consisting of:
antimony trifluoride in the presence of antimony pentachloride;
antimony pentafluoride;
antimony chlorofluorides of the general formula $SbCl_{5-x}F_x$ where X is 1 or mixture of SbCl$_3$ and SbCl$_5$, AlF$_3$, CrF$_3$, FeCl$_3$, SnCl$_4$, MoCl$_5$, WCl$_6$, more; metal fluorides KF, NaF, AgF, HgF$_2$, TaF$_5$, or NbF$_5$; and
hydrogen fluoride along or in the presence of catalytic amounts of SbCl$_5$, a TICl$_4$, ZrCl$_4$, HfCl$_4$, TaF$_5$, or NbF$_5$.

* * * * *